(12) United States Patent
Uezumi et al.

(10) Patent No.: US 6,632,359 B1
(45) Date of Patent: Oct. 14, 2003

(54) BLOOD PURIFYING APPARATUS

(75) Inventors: Satoshi Uezumi, Oita (JP); Makoto Yoshida, Oita (JP)

(73) Assignee: Asahi Medical Co., Ltd., Tokyo (JP)

( * ) Notice: Subject to any disclaimer, the term of this patent is extended or adjusted under 35 U.S.C. 154(b) by 0 days.

(21) Appl. No.: 09/831,311

(22) PCT Filed: Nov. 9, 1999

(86) PCT No.: PCT/JP99/06224

§ 371 (c)(1),
(2), (4) Date: May 8, 2001

(87) PCT Pub. No.: WO00/27447

PCT Pub. Date: May 18, 2000

(30) Foreign Application Priority Data

Nov. 9, 1998 (JP) .............................. 10-317877
Nov. 9, 1998 (JP) .............................. 10-317935

(51) Int. Cl.$^7$ ......................... B01D 63/02; B01D 69/08
(52) U.S. Cl. ........................... 210/500.23; 210/321.78; 210/321.87
(58) Field of Search ...................... 210/321.78, 321.79, 210/321.8, 321.87, 321.88, 321.89, 500.21, 500.23

(56) References Cited

U.S. PATENT DOCUMENTS

| 3,896,061 | A | * | 7/1975 | Tanzawa et al. | |
| 4,134,837 | A | * | 1/1979 | Yamashita et al. | 210/500.21 |
| 4,269,713 | A | * | 5/1981 | Yamashita et al. | 210/500.21 |
| 4,439,322 | A | * | 3/1984 | Sonoda et al. | 210/500.21 |
| 4,906,375 | A | | 3/1990 | Heilmann | 210/500.23 |
| 5,624,561 | A | * | 4/1997 | Uenishi et al. | 210/500.32 |
| RE37,759 | E | * | 6/2002 | Belfort | 210/636 |

FOREIGN PATENT DOCUMENTS

| EP | 0 842 694 | 5/1998 |
| JP | 58-091806 | 5/1983 |
| JP | 61-268304 | 11/1986 |
| JP | 03-161031 | 7/1991 |
| JP | 06-262046 | 9/1994 |
| JP | 09-308684 | 12/1997 |
| JP | 10-121324 | 5/1998 |
| JP | 10-165774 | 6/1998 |

\* cited by examiner

*Primary Examiner*—John Kim
(74) *Attorney, Agent, or Firm*—Young & Thompson

(57) ABSTRACT

A blood purifying apparatus having excellent purification performance (elimination of low molecular proteins, etc.) and being contaminated with little endotoxins flowing from the dialyzate side is described. Attention was paid to the solute permeability coefficient α and water permeability performance Lp of blood purifying apparatus and the relation between α and Lp has been examined. As a result, a blood purifying apparatus having excellent purification performance and substantially being free from invasion of endotoxins was obtained by regulating the value α/Lp to $6×10^{-7}$ or above, or regulating α within a range of $8×10^5$ to $1.5×10^{-3}$, and the value α×Lp to $2.4×10^{-2}$ or less. Also, a blood purifying apparatus having excellent purification performance and substantially being free from invasion of endotoxins was obtained by regulating the invasion ratio which is obtained by the polymer invasion test to 10% or less.

12 Claims, No Drawings

BLOOD PURIFYING APPARATUS

TECHNICAL FIELD

The present invention relates to a blood purifying apparatus with high blood treating capabilities such as elimination of low molecular proteins and the like, and, particularly, to a blood purifying apparatus with reduced inflow of endotoxins from the dialyzate side.

BACKGROUND ART

Conventionally, a blood purifying apparatus used for hemodialysis, hemofiltration, and the like has an object of removing metabolic decomposition products and toxic substances accumulated in the blood by applying principle of diffusion or filtration. After development of a drum-type hemodialyzer by Kolff et al. in 1943, for example, membrane type dialyzers have been used for the therapy of patients who have partially or completely lost kidney function.

Metabolic decomposition products and toxic substances are generally eliminated through a membrane. Membranes made of regenerated cellulose or synthetic polymer such as polyethylene, polyacrylonitrile, polysulfone, or the like are known in the art. These materials are fabricated into membranes in the form of a sheet or hollow fiber. The hollow fiber membranes have become more popular in recent years due to the large blood contact area and high processing capacity.

If the membrane is in the form of a sheet, two or more sheets are layered and-filled into a plastic container; if hollow fibers, several hundred to several tens of thousands of pieces of fiber are bundled and filled into a cylindrical plastic container to make semi manufactured goods, which is sterilized and used as blood purifying apparatus. When processing blood using a hollow fiber blood purifying apparatus, blood is caused to flow inside hollow fibers and a dialyzate containing an inorganic electrolyte and the like is caused to flow outside the hollow fibers. Substances to be eliminated from blood are diffused or filtered through the hollow fiber membrane to the dialyzate side.

In the early stage, the materials to be eliminated by blood treatment other than water retained in the body were low molecular weight inorganic substances such as urea nitrogen, creatinine, uric acid, and the like. In 1965, Scribner proposed, in his middle molecular hypothesis, that it is necessary to eliminate substance having a certain large molecular weight for the maintenance of a normal state in patients who have lost kidney function. In the later half of the 1980's, β2 microglobulin (hereinafter referred to as $\beta_2$-Mg) which is a protein with an estimated molecular weight of 11,200 was found in the arthrogenous area of a patient exhibiting dialysis amyloidosis which is a typical symptom of long-term dialysis patients. For these reasons, the recent main stream is a high performance blood purifying apparatus which is designed to eliminate low molecular weight proteins having a molecular weight from about ten thousand to several tens of thousands.

The intended elimination of low molecular weight proteins such as $\beta_2$-Mg requires expansion of membrane pore sizes to a certain degree. Excessive pore size expansion, however, accompanies problems such as escape of albumin (molecular weight: 66,000), which is a useful protein, and reverse filtration of dialyzate from the outside of the hollow fibers to the inside where the blood flows. This may allow invasion of a very small amount of endotoxins contained in the dialyzate into the blood side and may cause anaphylactogenic symptoms. Therefore, in many clinical facilities an endotoxin adsorbent or an endotoxin elimination filter are provided immediately before the dialyzate side entrance of the dialyzer to control the dialyzate.

In dialyzers using an advanced high performance technology, however, these known technologies may encounter difficulties in sufficiently preventing the effect of endotoxins when the endotoxin elimination filter and the like deteriorate or joints of dialyzate lines and the dialyzer are contaminated.

DISCLOSURE OF THE INVENTION

An object of the present invention is to provide a blood purifying apparatus having excellent blood-purification performance such as elimination performance of low molecular proteins and the like, and allowing only reduced inflow of endotoxins from the dialyzate side.

The inventors of the present invention have conducted extensive studies on the membrane structure and characteristics, and found that, even in a blood purifying apparatus with high elimination performance of low molecular weight proteins, it is possible to remarkably decrease endotoxin inflow from the dialyzate side by adjusting the membrane characteristics within certain specific values. This finding has led to the completion of the invention.

Specifically, an object of the present invention is to provide a blood purifying apparatus in which (1) the value obtained by dividing the solute permeability coefficient ($\alpha$ value) which is obtained by the penetration test of a high weight moleculas substance, by the water permeability performance (Lp value) is $6 \times 10^{-7}$ or more, (2) the solute permeability coefficient ($\alpha$ value) is in the range of $8 \times 10^{-5}$ to $1.5 \times 10^{-3}$ and the product of the solute permeability coefficient ($\alpha$ value) and the water permeability performance (Lp value), which is obtained by the polymer penetration test, is $2.4 \times 10^{-2}$ or less, or (3) the invasion ratio obtained by the invasion test of a high molecular weight substance is 10% or less.

Another object of the present invention is to provide a blood purifying apparatus satisfying two or more of the above three conditions at the same time.

Still another object of the present invention is to provide a blood purifying apparatus satisfying any of the following conditions: the Lp value is in the range of 50 ml/Hr/mmHg/m² to 170 ml/Hr/mmHg/m²; an s value obtained by the invasion test of a high molecular weight substance is in the range of 1,000 to 5,000 and/or a p value obtained by the invasion test of a high molecular weight substance is 6% or less; and the blood purifying apparatus is made from an asymmetric hollow fiber membrane.

The blood purifying apparatus in the present invention is an artificial kidney which eliminates insoluble component in the blood by dialysis and/or filtration by causing the blood to contact with a dialyzate via a membrane such as a hemodialyzer, hemofilter, hemodialyis-filter, and the like.

The penetration test of high-molecular substance in the present invention is a test comprising causing a solution of a water soluble substance with a known high molecular weight to flow into the dialyzate side and detecting the amount of the dissolved substance permeating into the blood side through the membrane. Polyvinylpyrrolidone (hereinafter referred to as PVP) is used as the solute. PVP having a molecular weight distribution in the range of several thousand to about 300,000 which is made available by BASF under the trademark PVP(K-30) for example, is suitable for use in a test such as the present test in which the object of evaluation is permeability of proteins with a molecular weight of about several tens of thousand or permeability of endotoxins with a molecular weight of about several hundred of thousands. In the present test, PVP having a weight average molecular weight of 35,000 is used after confirming the molecular weight distribution using HPLC. The PVP may be from a single production lot or, if the molecular weight significantly differs from 35,000, two or more lots may be mixed to adjust the molecular weight distribution.

The method of conducting this test will now be described. A 20 ppm PVP solution is prepared using PVP with a known molecular weight and is fed to a blood purifying apparatus after discharge of a washing liquid used for previous washing according to a normal washing procedure. The PVP solution is caused to filtrate wholly from the dialyzate side to the blood side of the blood purifying apparatus at a rate of 100 ml/minute. The pressure difference between the dialyzate side and the blood side after five minutes from start of filtration is assumed to be $\Delta P$ (mmHg) The amount of the PVP solution obtained from the blood side for the duration of one minute after five minutes have elapsed from the start of filtration is measured, and the content of PVP in the solution is quantitatively determined by HPLC.

$$\text{Permeability (\%)} = 100 \times \text{Blood side exit concentration} \div \text{Initial fluid concentration} \quad (1)$$

Lp in the present invention is the value defined by the following formula (2). In the following formula (2), V (ml/min) is the amount of PVP solution flowing out from the blood side exit during a period of one minute after five minutes have elapsed from the start of filtration.

$$Lp \text{ (ml/Hr/mmHg/m}^2\text{)} = V \times 60 \div \Delta P \div \text{Membrane area} \quad (2)$$

The membrane area herein indicates the effective internal area (m$^2$) of the blood purifying apparatus. α in the present invention indicates the value defined by the following formula (3).

$$\alpha = \text{Permeability} \div Lp \div \Delta P \quad (3)$$

The value α in this test is a parameter indicating the degree of ease with which the high molecular substances move from the dialyzate side into the blood side. In general, a larger value α is preferable for increasing the efficiency of eliminating urinary poisonous substances from the body because the capability of a membrane of eliminating a solute from the blood side to the dialyzate side has a positive correlation with the permeability of the solute from the dialyzate side to the blood side. However, an excessively large value α accompanies an increase in the amount of toxic substances such as endotoxins moving into the blood side from the dialyzate side, which may induce anaphylactogenic symptoms.

Therefore, the inventors of the present invention have paid attention to both the solute permeability coefficient α and the water permeability performance Lp, and have conducted extensive studies on the relationship between the values of α and Lp in the development of manufacturing conditions and structure of membrane. As a result, the inventors have found that if the value (α/Lp) obtained by dividing a by Lp is $6 \times 10^{-7}$ or greater, a blood purifying apparatus (even if it is designed so as to eliminate unwanted substances with a relatively large molecular weight from the blood) allows only a very limited amount of endotoxins to move from the dialyzate side. The effect is remarkable when the value α/Lp is $7.5 \times 10^{-7}$ or greater, and particularly when $9 \times 10^{-7}$ or greater. However, the value α/Lp should be less than $3 \times 10^{-5}$ to achieve dialysis with a sufficient water elimination capacity while causing albumin (molecular weight: 66,000), which is a useful substance in the blood, to permeate through the membrane in an amount as small as possible and minimizing invasion of endotoxins.

Although the reason that the blood purifying apparatus satisfying these conditions can achieve the object of the present invention is not necessarily clear, it is assumed that delicate control of membrane manufacturing conditions ensures a certain balance between the solute permeability and water permeability, resulting in the target membrane.

Blood purifying apparatus designed to exhibit a comparatively high water permeability are commonly used because of popular use of a UFR controller in the current dialysis treatment. In the blood purifying apparatus of the present invention, two contradictory problems, one, improvement in the capability for eliminating unnecessary substances, and the other, inhibition of endotoxin invasion, can be solved at the same time by setting the Lp value in the range of 50 ml/Hr/mmHg/m$^2$ to 170 ml/Hr/mmHg/m$^2$ and the α/Lp value above $6 \times 10^{-7}$ The range of 70 ml/Hr/mmHg/m$^2$ to 110 ml/Hr/mmHg/m$^2$ is more preferable for the value Lp.

In addition, if the α value, which is the permeability of a solute, is set at $8 \times 10^{-5}$ or above, while the above conditions are satisfied, the blood purifying apparatus may exhibit a greater capability for eliminating low molecular proteins and decreased inflow of endotoxins from the dialyzate side. A more preferable α value is $9 \times 10^{-5}$ or above, and particularly $10 \times 10^{-5}$ or above. The upper limit of the value α in practical use is $1.5 \times 10^{-3}$ from the viewpoint of the mechanical strength of the membrane.

Detailed investigation has revealed that a membrane with an asymmetric structure having dense layers in inner surfaces and having holes expanding toward the external surface achieves a greater capability of eliminating low molecular proteins than a uniform membrane in which the holes in both internal and external surfaces are uniform.

Moreover, a blood purifying apparatus with a value α greater than $8 \times 10^{-5}$ and the product of α and Lp (α·Lp) less than $2.4 \times 10^{-2}$ has been found to minimize endotoxin invasion, while achieving high performance in eliminating low molecular proteins. When the solute permeability coefficient α is less than $8 \times 10^{-5}$ also in this instance, the elimination performance of low molecular weight proteins, for example, $\beta_2$-Mg, is impaired, resulting in poor performance. If the pore size through which uremic substances permeate is expanded or the number of holes is increased to increase the α value, the value Lp which represents permeability of water increases. If the product of Lp and α is greater than $2.4 \times 10^{-2}$, endotoxins in the dialyzate tends to invade. Therefore, a preferable value of α is $9 \times 10^{-5}$ or above, and particularly $10 \times 10^{-5}$ or above. The upper limit of the value α should be $1.5 \times 10^{-3}$ from the viewpoint of ensuring mechanical strength. The reason is considered to be that too many holes in the membrane may impair the strength.

A more preferable blood purifying apparatus will be achieved if the value Lp is in the range of 50 to 170 ml/Hr/mmHg/m$^2$, the value α is above $8 \times 10^{-5}$, and the product of Lp and α is $2.4 \times 10^{-2}$ or less. Moreover, a blood purifying apparatus with even better performance is expected if the value Lp is in the range of 70 to 110 ml/Hr/mmHg/m$^2$. If Lp is less than 50 ml/Hr/mmHg/m$^2$, water elimination performance may be insufficient, resulting in impaired elimination of low molecular proteins of which the major part should be eliminated by filtration. On the other hand, if Lp is greater than 170 ml/Hr/mmHg/m², back-filtration of water increases and the blood purifying apparatus tends to allow endotoxins in the dialyzate to invade the blood.

As a result of further investigation, the inventors have found that a blood purifying apparatus satisfying the ratio α/Lp in the range of $8\times10^7$ to $3\times10^5$ in addition to the above conditions exhibits more preferable performance. Specifically, it was discovered that the blood purifying apparatus not only exhibits performance excellent but also less invasion of endotoxins from the dialyzate side if the ratio α/Lp is greater than $8\times10^{-7}$. A more preferable value of the ratio α/Lp is from $10\times10^{-7}$ to $10\times10^{-5}$, with an optimum range being from $11\times10^{-7}$ to $3\times10^{-6}$. If the ratio α/Lp is less than $8\times10^{-7}$ or greater than $3\times10^{-5}$, it appears to be difficult to perform well-balanced dialysis in which the blood purifying apparatus exhibits sufficient water elimination performance while allowing only a minimal amount of albumin (molecular weight: 66,000), which is a useful substance in the blood, to pass through the membrane.

A invasion test of a high molecular substance in the present invention is a test for detecting invasion of PVP, with a weight average molecular weight of 35,000 used in the penetration test of a high molecular substance, by flowing a solution of PVP, from the dialyzate side into the blood side. The following procedure was adopted in the present invention to reflect a more practical dialysis treatment and evaluate the conditions immediately after initiation of dialysis.

Specifically, after filling the blood side with pure water, the entrance and exit of the blood are closed with forceps and the PVP solution is caused to flow through the dialyzate side at a rate of 500 ml/minute. Then, pure water is caused to flow through the blood side at a rate of 100 ml/minute and, at the same time, the forceps at the entrance and exit of the blood are eliminated. The amount of the discharged solution from the blood exit side is determined for one minute after pure water is caused to flow through the blood side. The total solution on the blood exit side is collected to determine the following characteristics of the blood purifying apparatus.

The invasion ratio in the present invention is obtained by a high molecular weight substance invasion test using the blood purifying apparatus and indicates the value calculated by the following formula (4).

$$\text{Invasion rate }(\%)=100\times(Qd\times Cd)/(Qb\times Cb) \quad (4)$$

wherein, Qd indicates the rate of inflow into the dialyzate side (ml/min), Qb indicates the rate of outflow from the blood side (ml/min), Cd indicates the concentration of liquid flowing into the dialyzate side (ppm), and Cb indicates the concentration of liquid flowing out from the blood side (ppm).

The invasion ratio here indicates a parameter indicating the ratio of PVP, a high molecular substance, invading the blood side to the total amount of PVP which is supplied to the dialyzate side.

Although a major proportion of PVP used in the present invention has a molecular weight of 35,000, the PVP molecular weight has a distribution ranging from several thousand to about 300,000. Therefore, the value p of the following formula can be determined by studying the data obtained from the invasion test of a high molecular weight substance in more detail, analyzing the chromatogram obtained by HPLC, and calculating the invasion ratio of PVP with different molecular weights.

To determine the value p of the present invention, the values defined by the following formula (5) is first determined.

$$s=(k1+k2)\times 20000\div 2 \quad (5)$$

wherein k1 indicates the invasion rate of a solute having a molecular weight of 20,000 and k2 indicates the invasion rate of a solute having a molecular weight of 40,000.

Then, the value p of the present invention is determined according to the following formula (6).

$$p=(k3+k4)\times 20000\div 2\div s\times 100 \quad (6)$$

wherein k3 indicates the invasion rate of a solute having a molecular weight of 50,000 and k4 indicates the invasion rate of a solute having a molecular weight of 70,000.

The value s in this test is a parameter indicating the degree of ease with which PVP with a molecular weight of 20,000 to 40,000 invades from the dialyzate side. On the other hand, the value p is a parameter indicating the ratio of the degree of ease with which PVP with a molecular weight of 50,000 to 70,000 invades from the dialyzate side to the values, which is a parameter indicating the degree of ease with which PVP with a molecular weight of 20,000 to 40,000 invades from the dialyzate side.

The present inventors have conducted detailed studies of the membrane manufacturing conditions and membrane structure, as well as the relation among the invasion ratio, s value, and p value. As a result, the inventors have found that if the invasion ratio is kept to 10% or less, the blood purifying apparatus permits only a limited amount of endotoxins to invade, notwithstanding the high performance of eliminating low molecular proteins. Because the invasion ratio cannot be a negative value, as is clear from the definition, the lower limit of the invasion ratio satisfying the subject problem is 0% or more.

The reason that the membrane satisfying these conditions can achieve the object of the present invention is assumed to be the fact that delicate control of the membrane manufacturing conditions ensures bringing permeability of the solute into a suitable range, resulting in the target membrane. However, the reason why the invasion ratio can be an effective parameter to endotoxin invasion is not necessarily clear. Endotoxin, which is a compound having a molecular weight of about 8,700 as minimum unit, is thought to be present in association, with two or more units and having a molecular weight of slightly less than 20,000 to several hundred of thousands. Therefore, if PVP with an average molecular weight of 50,000 is used and its invasion ratio is as much as several percent, a considerable amount of endotoxins is estimated to invade from the dialyzate side. Surprisingly, however, if endotoxin invasion is suppressed by maintaining the invasion ratio at 10% or less, this results in a dialyzer exhibiting substantially no invasion. A preferable range of the invasion ratio is 9% or less, with 8% or less being more preferable.

Moreover, it was discovered that more preferable results can be obtained if the value s, which is a parameter indicating the degree of ease with which PVP with a molecular weight of 20,000 to 40,000 invades from the dialyzate side, is maintained at 1,000 or more. Specifically, the solute permeability from the dialyzate side to the blood side represented by the value s was found to indicate the solute elimination characteristics from the blood side, which is inherent performance required for a dialyzer. As a consequence, the elimination performance of low molecular proteins from the blood is improved by maintaining the value sat 1,000 or above, thereby providing a more preferable resolution to the subject. Here, the greater the value s, the better the results because the value s also represents solute elimination characteristics from the blood. However, the maximum value of s should be 5,000 for the membrane to perform dialysis while minimizing the amount of permeating albumin which is a useful substance in the blood.

The range of the value s in the present invention is preferably 1,025 or more, and more preferably 1,050 or more.

In addition, more detailed analysis of the invasion ratio at a high molecular weight range revealed that more preferable results are available if a balance of the solute permeability of the dialyzer that is shown by the value p is within a certain range. Specifically, the low molecular protein elimination performance can be increased by maintaining the value p at 6% or less, resulting in a dialyzer with reduced endotoxin invasion, which is a target of the present invention. In the same manner as in the invasion ratio, the value p cannot be a negative value, as is clear from the definition. Its lower limit is therefore 0% or more. The range of the value P in the present invention is preferably 5.8% or less, and more preferably 5.5% or less.

The present inventors have conducted more detailed studies on the relationship among the values $\alpha$, Lp, the invasion ratio, s, and p. As a result, it was found that if the vale $\alpha$ is maintained in the range of $8 \times 10^{-7}$ to $3 \times 10^{-5}$, the product of $\alpha$ and Lp is less than $2.4 \times 10^{-2}$ and the invasion ratio is kept at 10% or less, the blood purifying apparatus permits only a limited amount of endotoxins to invade, notwithstanding the high performance in eliminating low molecular proteins. Here, because the invasion ratio cannot be a negative value, as is clear from the definition, the lower limit of the invasion ratio satisfying the subject problem is 0% or more.

Furthermore, more detailed analysis of the invasion ratio at a high molecular weight range in the blood purifying apparatus satisfying the above characteristics has revealed that more preferable results are obtained if a balance of the solute permeability of the blood purifying apparatus that is shown by the value p is within a certain range. Specifically, a value of p of 6% or less not only can improve the low molecular protein elimination performance of the blood purifying apparatus, but also ensure treatment without loss of albumin, which is a useful substance for the body, while permitting only a small amount of endotoxins to invade the blood side. Thus, an ideal blood purifying apparatus conforming to the objective of the present invention can be provided. In the same manner as in the invasion ratio, the value p cannot be a negative value, as is clear from the definition. Its lower limit is therefore 0% or more. The range of the value p in the present invention is preferably 5.8% or less, and more preferably 5.5% or less.

As a result of further detailed studies, a blood purifying apparatus with improved performance of eliminating low molecular proteins has been successfully achieved while permitting only a limited amount of endotoxins to invade, by maintaining the ratio $\alpha$/Lp, that is, the value $\alpha$ which is a solute permeability coefficient obtained by the polymer penetration test, divided by the value Lp (ml/Hr/mmHg/m$^2$) which is the water permeability performance, at $6 \times 10^{-7}$ or above, and by maintaining the invasion ratio at 10% or less; or by maintaining the ratio $\alpha$/Lp at $6 \times 10^{-7}$ or above, the value $\alpha$ in the range of $8 \times 10^7$ to $3 \times 10^{-5}$, the product of $\alpha$ and Lp at $2.4 \times 10^{-2}$ or less, and the invasion ratio at 10% or less.

There are no specific limitations to the material for the membrane used for the blood purifying apparatus of the present invention, so long as such a material is applicable to blood purification. Examples of such a material include regenerated cellulose membranes, polysulfone membranes in which a hydrophilic polymer, such as PVP, polyvinyl alcohol, polyethylene glycol, etc., is incorporated for providing hydrophilic properties, cellulose triacetate membranes, polymethylmethacrylate membranes, polyacrylonitrile membranes, ethylene vinyl alcohol membranes, and the like. A particularly preferable example is a hollow fiber membrane made from polysulfone with PVP added thereto. Although the membrane may be of any form such as hollow fibers, a flat membrane, etc., hollow fibers are more preferable in order to enlarge the surface area with which the blood comes into contact.

The hollow fiber membrane made from polysulfone with PVP added thereto preferably used for blood purification in the present invention can be prepared by the following method, for example.

A spinning solution for the preparation of the membrane comprises 10 to 20 wt % of polysulfone, 2 to 12 wt % of PVP, and solvents for these polymers. Any solvent which can dissolve both polysulfone and PVP, such as dimethylacetamide, dimethylsulfoxide, N,N-dimethylformamide, N-methyl-2-pyrrolidone, etc. can be used either individually or as a mixture of two or more in any ratio. Water and the like may be added as a non-solvent of polysulfone to the extent the polymer does not precipitate.

In the membrane manufacturing process, after formation of polysulfone nuclei due to dispersion of the solvent and immersion in the non-solvent from the spinning solution, aggregate particles are produced with PVP being present on the surface. Hollow fiber membranes with a dense layer formed on the side that comes into contact with the blood and a supporting layer formed on the other side are thus produced. The membrane used for the blood purifying apparatus of the present invention preferably has a comparatively small number of large pores in the dense layer. For this reason, the rate of formation of the polysulfone aggregate particles should preferably be controlled in the process of membrane manufacturing.

The present inventors have found that a blood purifying apparatus by which the object of the present invention is achieved can be provided by manufacturing a hollow fiber membrane under stringently controlled conditions.

Specifically, the hollow fiber membrane for the blood purifying apparatus of the present invention which satisfies the requirement for the ratio $\alpha$/Lp of $6 \times 10^{-7}$ or above can be obtained by controlling the viscosity of the spinning solution in the range of 1,200 to 3,500 mPa·s, the concentration of a hydrophobic component, for example, dimethylacetamide, at 30% or higher, and the drafting ratio in the range of 1.1 to 1.9 in a known method of manufacturing hollow fiber membranes.

The hollow fiber membrane for the blood purifying apparatus which satisfies the requirements of the value $\alpha$ in the range of $8 \times 10^{-5}$ to $1.5 \times 10^{-3}$ and the ratio $\alpha$/Lp of $2.4 \times 10^{-2}$ or less can be obtained by controlling the viscosity of the spinning solution in the range of 2,800 to 3,100 mPa·s by using a large proportion of hydrophilic components such as PVP and water to hydrophobic components, with the drafting ratio in the range of 1.4 to 1.6. In this instance, a favorable result is obtained if the ratio of polysulfone/PVP in raw membrane solution is less than 1.7.

The hollow fiber membrane for the blood purifying apparatus of the present invention satisfying the conditions for an invasion ratio of less than 10% can be manufactured by applying the same conditions as above with respect to the spinning solution, viscosity, and drafting ratio. To achieve a more preferable invasion ratio, the water content in the spinning solution should be reduced (to as low as 1%, for example) or the water content in the hollow space producing agent should be decreased.

The resulting hollow fiber membranes which satisfy these specific various conditions are processed by a known method to obtain hollow fiber membrane bundles. Specifically, the hollow fiber membranes are wound around a reel, cut into a prescribed length, and washed with hot water. Then, a holder for a pore dimension such as an aqueous solution of glycerol is attached, followed by drying under vacuum.

The resulting hollow fiber membrane bundles are filled into a cylindrical plastic container, both ends are secured by adhesion with a potting agent, both terminals are cut, and the container is capped, thereby providing a half-finished product. The blood purifying apparatus of the present invention is obtained by attaching a plug to the half-finished product, as required, and sterilizing the container. It is possible to fill the half-finished product container with pure water or a solution of a water-soluble substance such as sodium pyrosulfite, acetone sodium bisulfite, etc., then plug and sterilize the container. Sterilization with ethylene oxide gas or high pressure steam, sterilization with radiation such as γ-ray, and the like can be arbitrarily used as the method of sterilization.

The blood purifying apparatus thus manufactured exhibits high performance such as elimination of low molecular proteins and the like, while allowing substantially no endotoxins to invade from the dialyzate side.

Best Mode for Carrying out the Invention

The present invention will be described in more detail by examples and comparative examples, which are not intended to be limiting of the present invention.

The penetration test and invasion test of a high molecular weight substance, plasma performance evaluation test, and endotoxin test (ET test) in the examples and comparative examples were carried out as follows. In all tests, a washing operation was carried out using the same physiological saline solution and the like as used in the dialysis. After discharging the washing solution, the following procedure was performed.

PVP of which the weight average molecular weight was confirmed to be 35,000 by the measurement of molecular weight distribution using HPLC (LC9A manufactured by Shimazu Corp., analysis column, GF-310HQ manufactured by Showa Denko K. K.) was used for the penetration test and the invasion test of high molecular weight substance.

<Penetration Test of a High Molecular Weight Substance>

PVP (K-30 manufactured by BASF) was used as a solute component, and a 20 ppm aqueous solution of PVP was prepared for the determination of α, Lp, and ΔP. The aqueous PVP solution was caused to filtrate wholly from the dialyzate side to the blood side at a flow rate of 100 ml/min. The pressure difference ΔP (mmHg) between the dialyzate side and the blood side five minutes after initiation of filtration was determined. The amount of PVP solution obtained from the blood side during the period of one minute after five minutes had elapsed from the start of filtration was measured, and the content of PVP in the solution was quantitatively determined by HPLC (LC9A manufactured by Shimazu Corp., analysis column, GF-310HQ manufactured by Showa Denko K. K.). Permeability ratio was calculated by use of the above formula (1).

The value Lp (ml/Hr/mmHg/m$^2$) was calculated by applying the flow rate V (ml/min) of the PVP solution flowing out from the blood side exit during the period of one minute after five minutes had elapsed from the initiation of filtration, and the pressure difference ΔP before and after the membrane to the above formula (2).

Furthermore, the value α was determined from the above formula (3).

<Invasion Test of High Molecular Weight Substance>

As a solute component, a 20 ppm aqueous solution of PVP (K-30 manufactured by BASF) was prepared. Measurement of the invasion ratio was carried out according to the following procedure. Specifically, after filling the blood side with pure water, the entrance and exit for the blood were closed with forceps and the PVP solution was caused to flow through the dialyzate side at a rate of 500 ml/minute. After three minutes, pure water was caused to flow through the blood side at a rate of 100 ml/min and, at the same time, the forceps closing the entrance and exit for the blood were removed. The flow rate on the blood exit side one minute after the pure water was caused to flow through the blood side was measured and the total solution on the blood exit side was collected. The concentration of PVP in the solution flowing from the blood side was determined by HPLC (LC9A manufactured by Shimazu Corp., analysis column, GF-310HQ manufactured by Showa Denko K. K.), and the invasion ratio was calculated by applying the PVP concentration on the blood side and the original PVP concentration (20 ppm) to the formula (4)

The invasion ratio by molecular weight was determined by calculating the raw solution concentration and the blood exit side concentration for each molecular weight from the GPC column calibration curve, then calculating the value s and the value p respectively from the above formulas (5) and (6).

<Plasma Performance Evaluation Test>

($\beta_2$-Mg Clearance)

The performance evaluation was carried out in accordance with the method of the Japanese Society for Dialysis Therapy by causing cattle plasma (37° C., total protein content: 6.5 g/dl) in which $\beta_2$-Mg had been dissolved at a concentration of 1 mg/L to flow through the blood side at a flow rate of 200 ml/min for 60 minutes, then causing the dialyzate to flow through the dialyzate side at a flow rate of 500 ml/min. The flow rate of the filtrate per unit membrane area was 10 ml/min. 5 ml of plasma sample was collected from the plasma entrance side and exit side seven minutes after the dialyzate began to flow. The concentration of $\beta_2$-Mg in plasma was determined using imzain $\beta_2$-Mg (manufactured by Fuji Rebio Inc.) and the clearance was calculated according to the following formula (7).

$$\text{Clearance (ml/min)} = (Cbi - Cbo) \div Cbi \times Qbi \tag{7}$$

wherein Cbi indicates the concentration of solute at the entrance on the blood side, Cbo indicates the concentration of solute at the exit on the blood side, and Qbi indicates the flow rate at the entrance on the blood side (ml/min)

(Albumin sieving coefficient)

In accordance with the method of the Japanese Society for Dialysis Therapy cattle plasma (37° C., total protein content: 6.5 g/dl) was caused to flow through the blood side at a flow rate of 200 ml/min for 60 minutes, then the flow rate of the filtrate per unit membrane area was set at 10 ml/min, without causing the dialyzate to flow. Plasma samples at the plasma entrance side and exit side, and a sample of filtrate, 5 ml each, were collected seven minutes after the flow rate of the filtrate was controlled. The albumin concentration in the samples was determined by the laser nephelometry method and the albumin sieving coefficient was calculated according to the following formula (8).

$$\text{Sieving coefficient} = 2Cf \div (Cbi + Cbo) \tag{8}$$

wherein Cf indicates the concentration of solute at the filtrate side, Cbi indicates the concentration of solute at the entrance on the blood side, and Cbo indicates the concentration of solute at the exit on the blood side.

(ET test)

Cattle plasma (37° C., total protein content: 6.5 g/dl) was caused to flow through the blood side at a flow rate of 100 ml/min. Then, the cattle plasma flow was stopped, and the blood side entrance and exit were closed by forceps. After causing a dialyzate (37° C.), with endotoxins having been added in advance, was caused to flow through the dialyzate side at a rate of 500 ml/min for five minutes, the forceps on the blood side were removed and the cattle plasma was caused to flow at a flow rate of 100 ml/min. One minute after the cattle plasma was caused to flow, 5 ml of plasma discharged from the blood exit side was collected. Although the endotoxin concentration in a dialyzate used for clinical purpose is usually kept at a low level, the dialyzate used for the evaluation of the effect of the present invention was prepared by mixing a concentrated endotoxin solution which was prepared by leaving tap water at 37° C. for several days and a commercially available dialyzate, and adjusting the concentration to 5000 EU/L using Endospacy (ES-50 manufactured by Seikagaku Corp.). Et test was carried out using the dialyzate. The plasma obtained was treated by the PCA process to eliminate proteins and the endotoxin concentration in the plasma was determined using Endospacy (ES-50 manufactured by Seikagaku Corp.).

EXAMPLE 1

17 wt % of polysulfone ("P-1700" manufactured by AMOCO) and 9 wt % of PVP ("K-90" manufactured by ISP) were dissolved in 74 wt % of dimethylacetamide, and the solution was stirred for 10 hours to obtain a spinning solution for the manufacture of a membrane. The viscosity of the spinning solution was 2400 mPa·s at 45° C. Using a 30% aqueous solution of dimethylacetamide as a hollow space producing agent, the spinning solution was injected from annular nozzles with a slit width of 59.5 μm and run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 45.5 m/min and the drafting rate was 1.1. Hollow fiber bundles thus wound around a reel were cut and washed with hot water at 80° C. for 2 hours. The fiber bundles was adhered with glycerol aqueous solution and then dried under vacuum.

10,000 pieces of the hollow fiber membrane thus obtained was bundled and inserted into a cylindrical plastic container. Both ends of the hollow fibers were secured to the container using a polyurethane resin adhesive and the excess ends were cut off. A cap for introducing blood was provided, thereby providing a module with an effective length of 25 cm. γ-rays at a dose of 25 kGy were applied to obtain the blood purifying apparatus (effective membrane area: 1.5 m$^2$) of the present invention.

The penetration test and invasion test of a high molecular weight substance, ET test, and plasma performance evaluation test were carried out using the obtained blood purifying apparatus. The results are shown in Table 1.

EXAMPLE 2

17 wt % of polysulfone ("P-1700" manufactured by AMOCO) and 10 wt % of PVP ("K-90" manufactured by ISP) were dissolved in 73 wt % of dimethylacetamide, and the solution was stirred for 10 hours to obtain a spinning solution for the manufacture of a membrane. The viscosity of the spinning solution was 2650 mPa·s at 45° C. Using a 35% aqueous solution of dimethylacetamide as a hollow space producing agent, the spinning solution was injected from annular nozzles with a slit width of 59.5 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 26.3 m/min and the drafting rate was 1.9. Hollow fiber bundles thus wound around a reel were processed in the same manner as in Example 1 to obtain the blood purifying apparatus (effective membrane area: 1.5 m$^2$) of the present invention.

The penetration test and invasion test of a high molecular weight substance, ET test, and plasma performance evaluation test were carried out using the obtained blood purifying apparatus. The results are shown in Table 1.

EXAMPLE 3

18 wt % of polysulfone ("P-1700" manufactured by AMOCO) and 9 wt % of PVP ("K-90" manufactured by ISP) were dissolved in 73 wt % of dimethylacetamide, and the solution was stirred for 10 hours to obtain a spinning solution for the manufacture of a membrane. The viscosity of the spinning solution was 3320 mPa·s at 45° C. Using a 32% aqueous solution of dimethylacetamide as a hollow space producing agent, the spinning solution was injected from annular nozzles with a slit width of 59.5 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 38.5 m/min and the drafting rate was 1.3. Hollow fiber bundles thus wound around a reel were processed in the same manner as in Example 1 to obtain the blood purifying apparatus (effective membrane area: 1.5 m$^2$) of the present invention.

The penetration test and invasion test of a high molecular weight substance, ET test, and plasma performance evaluation test were carried out using the obtained blood purifying apparatus. The results are shown in Table 1.

EXAMPLE 4

18 wt % of polysulfone ("P-1700" manufactured by AMOCO) and 9 wt % of PVP ("K-90" manufactured by ISP) were dissolved in 73 wt % of dimethylacetamide, and the solution was stirred for 10 hours to obtain a spinning solution for the manufacture of a membrane. The viscosity of the spinning solution was 3200 mPa·s at 45° C. Using a 35% aqueous solution of dimethylacetamide as a hollow space producing agent, the spinning solution was injected from annular nozzles with a slit width of 59.5 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 27.8 m/min and the drafting rate was 1.8. Hollow fiber bundles thus wound around a reel were processed in the same manner as in Example 1 to obtain the blood purifying apparatus (effective membrane area: 1.5 m²) of the present invention.

The penetration test and invasion test of a high molecular weight substance, ET test, and plasma performance evaluation test were carried out using the obtained blood purifying apparatus. The results are shown in Table 1.

EXAMPLE 5

16 wt % of polysulfone ("P-1700" manufactured by AMOCO) and 10 wt % of PVP ("K-90" manufactured by ISP) were dissolved in 72 wt % of dimethylacetamide and 2 wt % of water, and the solution was stirred for 10 hours to obtain a spinning solution for the manufacture of a membrane. The viscosity of the spinning solution was 2800 mPa·s at 45° C. Using a 35% aqueous solution of dimethylacetamide as a hollow space producing agent, the spinning solution was injected from annular nozzles with a slit width of 59.5 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 35.7 m/min and the drafting rate was 1.4. Hollow fiber bundles thus wound around a reel were processed in the same manner as in Example 1 to obtain the blood purifying apparatus (effective membrane area: 1.5m²) of the present invention.

The penetration test and invasion test of a high molecular weight substance, ET test, and plasma performance evaluation test were carried out using the obtained blood purifying apparatus. The results are shown in Table 1.

EXAMPLE 6

16 wt % of polysulfone ("P-1700" manufactured by AMOCO) and 10 wt % of PVP ("K-90" manufactured by ISP) were dissolved in 73 wt % of dimethylacetamide and 1 wt % of water, and the solution was stirred for 10 hours to obtain a spinning solution for the manufacture of a membrane. The viscosity of the spinning solution was 2700 mPa·s at 45° C. Using a 35% aqueous solution of dimethylacetamide as a hollow space producing agent, the spinning solution was injected from annular nozzles with a slit width of 59.5 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 33.3 m/min and the drafting rate was 1.5. Hollow fiber bundles thus wound around a reel were processed in the same manner as in Example 1 to obtain the blood purifying apparatus (effective membrane area: 1.5 m²) of the present invention.

The penetration test and invasion test of a high molecular weight substance, ET test, and plasma performance evaluation test were carried out using the obtained blood purifying apparatus. The results are shown in Table 1.

EXAMPLE 7

15 wt % of polysulfone ("P-1700" manufactured by AMOCO) and 11 wt % of PVP ("K-90" manufactured by ISP) were dissolved in 72 wt % of dimethylacetamide and 2 wt % of water, and the solution was stirred for 10 hours to obtain a spinning solution for the manufacture of a membrane. The viscosity of the spinning solution was 3100 mPa·s at 45° C. Using a 35% aqueous solution of dimethylacetamide as a hollow space producing agent, the spinning solution was injected from annular nozzles with a slit width of 59.5 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 31.3 m/min and the drafting rate was 1.6. Hollow fiber bundles thus wound around a reel were processed in the same manner as in Example 1 to obtain the blood purifying apparatus (effective membrane area: 1.5 m²) of the present invention.

The penetration test and invasion test of a high molecular weight substance, ET test, and plasma performance evaluation test were carried out using the obtained blood purifying apparatus. The results are shown in Table 1.

EXAMPLE 8

15 wt % of polysulfone ("P-1700" manufactured by AMOCO) and 11 wt % of PVP ("K-90" manufactured by ISP) were dissolved in 72 wt % of dimethylacetamide and 2 wt % of water, and the solution was stirred for 10 hours to obtain a spinning solution for the manufacture of a membrane. The viscosity of the spinning solution was 3100 mPa·s at 45° C. Using a 35% aqueous solution of dimethylacetamide as a hollow space producing agent, the spinning solution was injected from annular nozzles with a slit width of 59.5 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 35.7 m/min and the drafting rate was 1.4. Hollow fiber bundles thus wound around a reel were processed in the same manner as in Example 1 to obtain the blood purifying apparatus (effective membrane area: 1.5 m²) of the present invention.

The penetration test and invasion test of a high molecular weight substance, ET test, and plasma performance evaluation test were carried out using the obtained blood purifying apparatus. The results are shown in Table 1.

EXAMPLE 9

17 wt % of polysulfone ("P-1700" manufactured by AMOCO) and 11 wt % of PVP ("K-90" manufactured by ISP) were dissolved in 72 wt % of dimethylacetamide, and the solution was stirred for 10 hours to obtain a spinning solution for the manufacture of a membrane. The viscosity of the spinning solution was 3600 mPa·s at 45° C. Using a 40% aqueous solution of dimethylacetamide as a hollow space producing agent, the spinning solution was injected from annular nozzles with a slit width of 59.5 μm and to run through a 50 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45 μm, the discharge linear velocity of the spinning solution was 26.3 m/min and the drafting rate was 1.9. Hollow fiber bundles thus wound around a reel were processed in the same manner as in Example 1 to obtain the blood purifying apparatus (effective membrane area: 1.5 m²) of the present invention.

The penetration test and invasion test of a high molecular weight substance, ET test, and plasma performance evaluation test were carried out using the obtained blood purifying apparatus. The results are shown in Table 1.

COMPARATIVE EXAMPLE 1

Using a 35% aqueous solution of dimethylacetamide as a hollow space producing agent, the same spinning solution as used in Example 9 was injected from annular nozzles with a slit width of 50 μm and to run through a 60 cm dry zone at a spinning rate of 50 m/min. Before being wound, the spun hollow fiber was passed through a coagulating bath that was placed below the spinning nozzle and filled with water. Because the amount of spinning solution injected was controlled so that the dry thickness of the hollow fiber membrane was 45μm, the discharge linear velocity of the spinning solution was 50.1 m/min and the drafting rate was 1.0. Hollow fiber bundles thus wound around a reel were processed in the same manner as in Example 1 to obtain the blood purifying apparatus (effective membrane area: 1.5 m) of the present invention.

The penetration test and invasion test of a high molecular weight substance, ET test, and plasma performance evaluation test were carried out using the obtained blood purifying apparatus. The results are shown in Table 1.

product of the solute transmission coefficient α and the water permeability performance Lp, which is obtained by the same test, is $2.4 \times 10^{-2}$ or less.

4. A blood purifying apparatus wherein a solute permeability coefficient α(Hr·m²/ml), which is obtained by a penetration test of a high molecular weight substance, is in a range of $8 \times 10^{-5}$ to $1.5 \times 10^{-3}$, and the product of the solute permeability coefficient α and the water permeability performance Lp (ml/Hr/mmHg/m²), which is obtained by said test, is in the range of more than 0 to $2.4 \times 10^{-2}$.

5. The blood purifying apparatus according to claim 4, wherein the water permeability performance Lp (ml/Hr/mmHg/m²) is in a range of 50 to 170.

6. A blood purifying apparatus in which an invasion ratio is obtained by an invasion test of a high molecular weight substance in a range of 0% to 10%.

7. The blood purifying apparatus according to claim 6, wherein the s value obtained by the invasion test is in a range of 1,000 to 5,000.

8. The blood purifying apparatus according to claim 6, wherein the p value obtained by an invasion test is in a range of 0% to 6%.

9. The blood purifying apparatus according to claim 6, wherein the solute permeability coefficient α(Hr·m²/ml) which is obtained by the penetration test of a high molecular weight substance, is in the range of $8 \times 10^{-5}$ to $1.5 \times 10^{-3}$, and the product of the solute permeability coefficient α and the water permeability performance Lp (ml/Hr/mmHg/m²), which is obtained by the same test, is $2.4 \times 10^{-2}$ or less.

10. The blood purifying apparatus according to claim 6, wherein the ratio α/Lp is in the range of $6 \times 10^{-7}$ to $3 \times 10^{-5}$

TABLE 1

| | α/Lp | Lp | α | α × Lp | Invasion rate | s | ρ | $\beta_2$-Mg clearance | Albumin sieving coefficient | ET concentration |
|---|---|---|---|---|---|---|---|---|---|---|
| Example 1 | $6.49 \times 10^{-7}$ | 203.3 | $1.32 \times 10^{-4}$ | $2.68 \times 10^{-2}$ | 11.6% | 1940.8 | 15.6% | 54.3 | 0.024 | 0.054 |
| Example 2 | $8.10 \times 10^{-7}$ | 192.5 | $1.56 \times 10^{-4}$ | $3.54 \times 10^{-2}$ | 12.4% | 6111.7 | 17.2% | 59.5 | 0.031 | 0.055 |
| Example 3 | $1.05 \times 10^{-6}$ | 167.9 | $1.77 \times 10^{-4}$ | $2.97 \times 10^{-2}$ | 16.6% | 5529.4 | 55.4% | 58.2 | 0.044 | 0.042 |
| Example 4 | $9.01 \times 10^{-7}$ | 163.2 | $1.47 \times 10^{-4}$ | $2.40 \times 10^{-2}$ | 15.4% | 3490.2 | 50.4% | 57.2 | 0.030 | 0.051 |
| Example 5 | $1.10 \times 10^{-6}$ | 110.4 | $1.21 \times 10^{-4}$ | $1.34 \times 10^{-2}$ | 9.7% | 5029.3 | 6.8% | 56.9 | 0.026 | 0.028 |
| Example 6 | $8.71 \times 10^{-7}$ | 108.1 | $9.42 \times 10^{-5}$ | $1.02 \times 10^{-2}$ | 7.6% | 1120.2 | 6.1% | 51.5 | 0.011 | 0.018 |
| Example 7 | $1.51 \times 10^{-6}$ | 119.5 | $1.81 \times 10^{-4}$ | $2.16 \times 10^{-2}$ | 9.1% | 4942.1 | 8.9% | 62.8 | 0.020 | 0.024 |
| Example 8 | $1.17 \times 10^{-6}$ | 88.9 | $1.04 \times 10^{-4}$ | $9.25 \times 10^{-3}$ | 5.8% | 1074.0 | 5.3% | 62.6 | 0.001 | 0.011 |
| Example 9 | $7.22 \times 10^{-6}$ | 108.1 | $7.81 \times 10^{-5}$ | $8.44 \times 10^{-3}$ | 5.4% | 669.4 | 0.6% | 49.8 | 0.012 | 0.009 |
| Comparative Example 1 | $5.60 \times 10^{-7}$ | 221.4 | $1.24 \times 10^{-4}$ | $2.75 \times 10^{-2}$ | 19.4% | 5681.3 | 28.9% | 56.2 | 0.048 | 0.551 |

Unit: Lp value  ml/Hr/mmHg/m²
     Invasion rate  %
     ρ value  %
     $\beta_2$-Mg clearance  ml/min
     ET concentration  EU/ml

What is claimed is:

1. A blood purifying apparatus wherein a ratio α/Lp is in a range of $6 \times 10^{-7}$ to $3 \times 10^{-5}$, said value obtained by a solute permeability coefficient α(Hr·m²/ml), which is obtained by a penetration test of a high molecular weight substance, being divided by water permeability performance Lp (ml/Hr/mmHg/m²) which is in a range of 50 to 170.

2. The blood purifying apparatus according to claim 1, wherein the solute permeability coefficient α is $8 \times 10^{-5}$ or more.

3. The blood purifying apparatus according to claim 1, wherein the solute permeability coefficient α, which is obtained by a penetration test of a high molecular weight substance, is in a range of $8 \times 10^{-5}$ to $1.5 \times 10^{-3}$, and the and the water permeability performance Lp (ml/Hr/mmHg/m²) is in a range of 50 to 170.

11. The blood purifying apparatus according to claim 1, comprising a hollow fiber membrane having an asymmetric structure.

12. The blood purifying apparatus according to claim 9, wherein the ratio α/Lp, a solute permeability coefficient α(Hr·m²/ml) which is obtained by the penetration test of a high molecular weight substance, being divided by water permeability performance Lp (ml/Hr/mmHg/m²), is $6 \times 10^{-7}$ or more.

* * * * *